US008895770B2

(12) United States Patent
Lewis et al.

(10) Patent No.: US 8,895,770 B2
(45) Date of Patent: *Nov. 25, 2014

(54) SELECTIVE NON-PRECIOUS METAL-CATALYZED MONO-HYDROSILYLATION POLYUNSATURATED COMPOUNDS

(75) Inventors: Kenrick M. Lewis, Flushing, NY (US); Aaron M. Tondreau, Zurich (CH); Richard W. Cruse, Yorktown Heights, NY (US); Keith J. Weller, Rensselaer, NY (US); Johannes G. P. Delis, Bergen op Zoom (NL); Susan A. Nye, Feura Bush, NY (US); Paul J. Chirik, Princeton, NJ (US)

(73) Assignees: Cornell University, Ithaca, NY (US); Momentive Performance Materials Inc., Waterford, NY (US)

( * ) Notice: Subject to any disclaimer, the term of this patent is extended or adjusted under 35 U.S.C. 154(b) by 198 days.

This patent is subject to a terminal disclaimer.

(21) Appl. No.: 13/302,506

(22) Filed: Nov. 22, 2011

(65) Prior Publication Data

US 2012/0130105 A1    May 24, 2012

Related U.S. Application Data

(60) Provisional application No. 61/417,061, filed on Nov. 24, 2010.

(51) Int. Cl.
*C07F 7/08* (2006.01)
*C07F 7/18* (2006.01)
*C07F 15/02* (2006.01)
*B01J 31/18* (2006.01)

(52) U.S. Cl.
CPC ............ *C07F 15/025* (2013.01); *B01J 31/1805* (2013.01)
USPC ............................ 556/456; 556/453; 556/482

(58) Field of Classification Search
CPC .. C07F 7/0829; C07F 7/0801; B01J 31/1815; B01J 31/1805
USPC ................... 502/155; 556/479, 456, 453, 482
See application file for complete search history.

(56) References Cited

U.S. PATENT DOCUMENTS

| | | | |
|---|---|---|---|
| 5,166,298 A | 11/1992 | Friedmann et al. | |
| 6,278,011 B1 | 8/2001 | Chen et al. | |
| 7,429,672 B2 | 9/2008 | Lewis et al. | |
| 7,696,269 B2 | 4/2010 | Cruse et al. | |
| 2011/0009565 A1 | 1/2011 | Delis et al. | |
| 2011/0009573 A1 | 1/2011 | Delis et al. | |
| 2012/0130106 A1* | 5/2012 | Chirik et al. ................. | 556/467 |

FOREIGN PATENT DOCUMENTS

| | | |
|---|---|---|
| WO | 2008/085453 | 7/2008 |
| WO | 2011/006044 | 1/2011 |
| WO | 2011/006049 | 1/2011 |

OTHER PUBLICATIONS

Bart et al., J. Am. Chem. Soc., 2004, 126, 13794-13807.
Archer et al., Organometallics, 2006, vol. 25, 4269-4278.
Wu et al., J. Am. Chem. Soc., vol. 132, 2010, p. 13214.
Kroll et al., Macromol. Chem. Phys. 2001, 202, No. 5, pp. 645-653.
Glatz et al., Journal of Chromatography A, 1015 (2003) 65-71.
Kim et al., Journal of Organometallic Chemistry 673 (2003) 77-83.
Pangborn et al., Journal of Organometallic Chemistry 15 (1996) 1518.

* cited by examiner

*Primary Examiner* — Yong Chu
(74) *Attorney, Agent, or Firm* — Joseph S. Ostroff, Esq.; McDonald Hopkins LLC

(57) ABSTRACT

Disclosed herein is the selective synthesis of mono-hydrosilylated derivatives of polyunsaturated compounds, such as trivinylcyclohexane using non-precious metal based pyridinediimine and terpyridine complex as selective hydrosilylation catalysts.

14 Claims, No Drawings

SELECTIVE NON-PRECIOUS METAL-CATALYZED MONO-HYDROSILYLATION POLYUNSATURATED COMPOUNDS

CROSS-REFERENCE TO RELATED APPLICATION

This application claims priority to U.S. provisional application No. 61/417,061, filed Nov. 24, 2010, which is herein incorporated by reference in its entirety.

FIELD OF THE INVENTION

This invention relates to the selective hydrosilylation of a single alkenyl or alkynyl group in a molecule having at least two unsaturated groups that can be hydrosilylated. In particular, this invention relates to the use of non-precious metal-based complexes as catalysts effective for mono-hydrosilylation of polyalkenyl compounds such as trivinylcyclohexane.

BACKGROUND OF THE INVENTION

Hydrosilylation of trivinylcyclohexane and similar alkenyl compounds with multiple carbon-carbon unsaturated bonds has been disclosed in, for example, U.S. Pat. Nos. 5,166,298, 6,278,011, 6,265,497, and 6,278,011. The emphasis in these patents has been on complete reaction of all double bonds. Accordingly, in the reactions disclosed in these patents, the molar ratios of the silicon hydride groups in the silyl hydrides relative to the carbon-carbon double bonds in the polyunsaturated compounds were greater than 1.0. In addition, long reaction times were often used to ensure complete hydrosilylation of the unsaturated groups.

Recently, the need for selective mono-hydrosilylation product of 1,2,4-trivinylcyclohexane has surfaced. Illustratively, U.S. Pat. No. 7,696,269 discloses that (2-trialkoxysilylethyl)divinyl-cyclohexane, which is a mono-hydrosilylation product of 1,2,4-trivinylcyclohexane, can be used as a key intermediate in the synthesis of sulfur silanes useful for imparting low rolling resistance to automobile tires.

Unfortunately, the selectivity of conventional precious metal based catalysts towards mono-hydrosilylation is normally less than desirable. For example, even when a sub-stoichiometric amount of silane is used in the platinum catalyzed hydrosilylation of trivinylcyclohexane (silane:vinyl ratio of 0.8:1), a mixture only containing about 50 weight percent of the desired mono-hydrosilylated product and about 30 weight percent of the bis-hydrosilylated derivative is produced.

Non-precious metal based hydrosilylation catalysts have been disclosed in the art. Illustratively, Wu et al. reported in J. Am. Chem. Soc. Vol 132 (2010) 13214 that low valent iron iminopyridine complexes catalyze 1,4-hydrosilylation of 1,3-dienes.

U.S. Patent Application Publication No. 20110009565 discloses non-precious metal terpyridine complexes and their use as hydrosilylation catalysts. U.S. Patent Application Publication No. 20110009573 discloses non-precious pyridine-diimine complexes and their use as hydrosilylation catalysts. The contents of the '565 and the '573 publications are incorporated herein by reference in their entireties. Although trivinylcyclohexane is among the unsaturated compounds mentioned in these two applications, the applications are silent regarding mono-hydrosilylation selectivity of the catalysts to polyunsaturated compounds such as trivinylcyclohexane.

Accordingly, there is a continuing need in the hydrosilylation industry for selectively producing mono-hydrosilylated product from a polyunsaturated compound and a silyl hydride. The present invention provides one answer to that need.

SUMMARY OF THE INVENTION

In one aspect, the present invention is directed to a process for selectively producing monosilylated reaction product from a composition containing a silyl hydride and a polyunsaturated compound. The process comprises contacting the composition, optionally in the presence of a solvent, with a complex of Formula (I), Formula (II) or Formula (III) to cause the silyl hydride to react with the polyunsaturated compound such that hydrosilylation occurs selectively at one unsaturated group of the unsaturated compound thereby producing the mono-hydrosilylation product, wherein the polyunsaturated compound is represented by Formula (IV) or Formula (V)

$$E^1[(CH_2)_\beta CR^1=CH_2]_\alpha, \quad \text{(Formula IV)}$$

$$R^2_\gamma E^2[(CH_2)_\beta CR^1=CH_2]_\alpha, \quad \text{(Formula V)}$$

wherein $E^1$ is a divalent or polyvalent aliphatic or aromatic cyclic hydrocarbon group containing from 3 to 25 carbon atoms, or a divalent or polyvalent aliphatic or aromatic heterocyclic hydrocarbon containing from 3 to 25 carbon atoms, wherein the heteroatom is selected from the group consisting of oxygen, nitrogen, silicon and sulfur;

$E^2$ is a divalent or polyvalent cyclic silicone group containing from 3 to 8 silicon atoms and from 3 to 8 oxygen atoms;

each occurrence of $R^1$ and $R^2$ is independently a hydrogen or a hydrocarbon group containing from 1 to 8 carbon atoms; and each occurrence of $\alpha$, $\beta$ and $\gamma$ is independently an integer, wherein $\alpha$ is 2 to 6; $\beta$ is 0 to 6; and $\gamma$ is 0 to 4;

wherein Formula (I), Formula (II) and Formula (III) are:

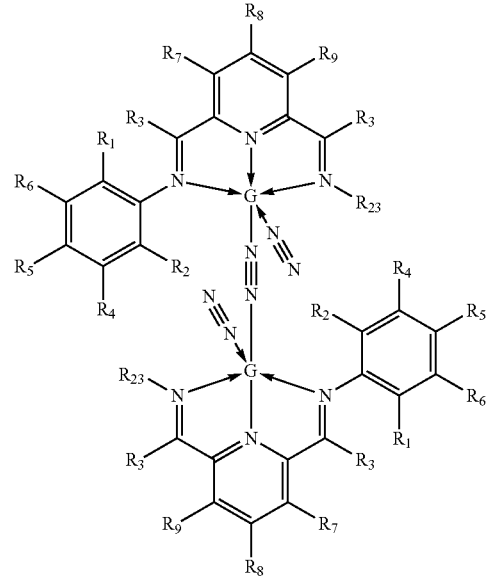

Formula (I)

-continued

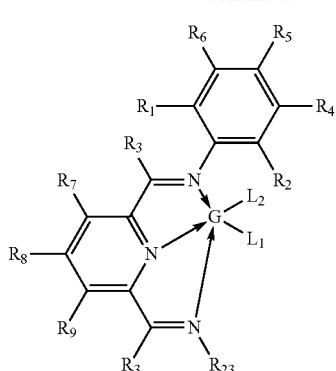

Formula (II)

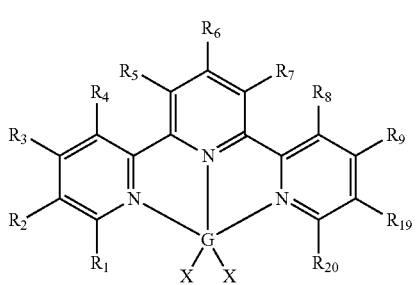

Formula (III)

wherein:

G is Mn, Fe, Ni, or Co;

each occurrence of $R_1$, $R_2$, $R_3$, $R_4$, $R_5$, $R_6$, $R_7$, $R_8$, $R_9$, $R_{19}$ and $R_{20}$ is independently hydrogen, C1-C18 alkyl, C1-C18 substituted alkyl, aryl, substituted aryl, or an inert functional group, wherein $R_1$ to $R_9$, $R_{19}$ and $R_{20}$, other than hydrogen, optionally contain at least one heteroatom;

each occurrence $R_{23}$ is independently C1-C18 alkyl, C1-C18 substituted alkyl, aryl or substituted aryl, wherein $R_{23}$ optionally contains at least one heteroatom;

optionally any two of $R_1$, $R_2$, $R_3$, $R_4$, $R_5$, $R_6$, $R_7$, $R_8$, $R_9$, $R_{19}$, $R_{20}$, and $R_{23}$ vicinal to one another taken together may form a ring being a substituted or unsubstituted, saturated, or unsaturated cyclic structure;

each of $L_1$ and $L_2$ is independently C1-C18 alkyl, C1-C18 substituted alkyl, aryl, substituted aryl, C2-C18 alkenyl, C2-C18 alkynyl, or $L_1$-$L_2$ together is one of the following Formula (A)

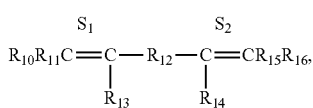

Formula (B)

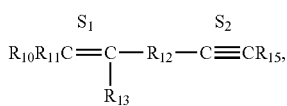

Formula (C)

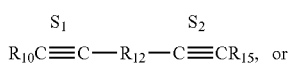

Formula (D)

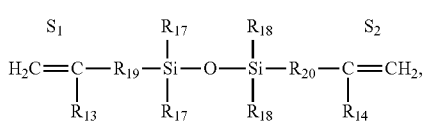

wherein each occurrence of $R_{10}$, $R_{11}$, $R_{13}$, $R_{14}$, $R_{15}$ and $R_{16}$ is independently hydrogen, C1-C18 alkyl, C2-C18 alkenyl, or C2-C18 alkynyl, wherein $R_{10}$, $R_{11}$, $R_{13}$, $R_{14}$, $R_{15}$ and $R_{16}$, other than hydrogen, optionally contain at least one heteroatom, and $R_{10}$, $R_{11}$, $R_{13}$, $R_{14}$, $R_{15}$ and $R_{16}$, other than hydrogen, are optionally substituted;

each occurrence of $R_{12}$ is independently C1-C18 alkyl, C1-C18 substituted alkyl, C2-C18 alkenyl, C2-C18 substituted alkenyl, C2-C18 alkynyl, C2-C18 substituted alkynyl, aryl, substituted aryl, wherein $R_{12}$ optionally contains at least one heteroatom;

optionally any two of $R_{10}$, $R_{11}$, $R_{12}$, $R_{13}$, $R_{14}$, $R_{15}$, $R_{16}$ taken together may form a ring being a substituted or unsubstituted, saturated or unsaturated cyclic structure;

each occurrence of $R_{17}$ and $R_{18}$ is independently alkyl, substituted alkyl, aryl, or substituted aryl, wherein each of $R_{17}$ and $R_{18}$ optionally contains at least one heteroatom, and wherein $R_{17}$ and $R_{18}$ taken together may form a ring being a substituted or unsubstituted, saturated or unsaturated cyclic structure;

each occurrence of $R_{19}$ and $R_{20}$ is independently a covalent bond that connects Si and C, an alkyl, substituted alkyl, or a heteroatom, wherein $R_{19}$, and $R_{20}$ optionally contain at least one heteroatom; wherein $L_1$-$L_2$ bonds with G through unsaturated sites $S_1$ and $S_2$;

each X is independently C1-C18 alkyl, C1-C18 substituted alkyl, aryl, or substituted aryl, wherein X optionally contains at least one heteroatom; and wherein the molar ratio of the Si—H groups in the silyl hydride to the alkenyl groups in the unsaturated compound is between about $(0.5/\alpha)$ and about $(1.1/\alpha)$.

In another aspect, the present invention is directed to a composition produced from the above described process, wherein the composition contains a mono-hydrosilylated product and a bis-hydrosilylated product; and wherein the gravimetric ratio of the mono-hydrosilylated product to the bis-hydrosilylated product is greater than about 1.8.

These and other aspects will become apparent upon reading the following description of the invention.

DETAILED DESCRIPTION OF THE INVENTION

This invention provides for the selective synthesis of mono-hydrosilylated derivatives of polyunsaturated compounds using non-precious metal based pyridinediimine and terpyridine complexes of Formula (I), Formula (II) or Formula (III) as described above.

Accordingly, in one embodiment, the present invention is directed to a process for the hydrosilylation of a composition containing a silyl hydride and a polyunsaturated compound. The process includes contacting the composition with a metal complex of Formula (I), Formula (II) or Formula (III), optionally in the presence of a solvent, to cause the silyl hydride to react with the polyunsaturated compound such that hydrosilylation occurs selectively at one unsaturated group of the polyunsaturated compound thereby producing the mono-hydrosilylation product containing the metal complex. The mono-hydrosilylation product can be subsequently recovered from the reaction mixture, for example, by distillation.

The polyunsaturated compound is represented by Formula (IV) or Formula (V)

$$E^1[(CH_2)_\beta CR^1=CH_2]_\alpha, \qquad \text{(Formula IV)}$$

$$R^2_\gamma E^2[(CH_2)_\beta CR^1=CH_2]_\alpha, \qquad \text{(Formula V)}$$

In connection with Formula (IV), $E^1$ is a divalent or polyvalent aliphatic or aromatic cyclic hydrocarbon group containing from 3 to 25 carbon atoms, or a divalent or polyvalent aliphatic or aromatic heterocyclic hydrocarbon group containing from 3 to 25 carbon atoms. Suitable heteroatom includes, but is not limited to, oxygen, nitrogen, silicon and sulfur. In one embodiment, $E^1$ contains from 4 to 20 carbon atoms. In another embodiment, $E^1$ contains from 4 to 15 carbon atoms. Exemplary $E^1$ includes aliphatic cyclic hydrocarbons such as cyclohexyl; aromatic cyclic hydrocarbons such as benzene ring; heterocyclic moiety such as a cyanurate, isocyanurate, or triazine ring. Advantageously, $E^1$ is cyclohexyl or a benzene ring.

In connection with Formula (V), $E^2$ is a divalent or polyvalent cyclic silicone group containing from 3 to 8 silicon atoms and from 3 to 8 oxygen atoms. Exemplary $E^2$ includes cyclotrisiloxane and cyclotetrasiloxane rings.

In connection with Formula (IV) and Formula (V), each occurrence of $R^1$ and $R^2$ is independently hydrogen or a hydrocarbon group containing from 1 to 8 carbon atoms. In one embodiment, $R^1$ is hydrogen or a C1-C4 alkyl group. In another embodiment, $R^2$ is hydrogen, a methyl or ethyl group.

Each occurrence of $\alpha$, $\beta$ and $\gamma$ is independently an integer. $\alpha$ has a value of from 2 to 6, preferably from 3 to 6; $\beta$ has a value from zero to 6, advantageously from zero to 2; and $\gamma$ has a value of from 0 to 4.

Examples of the polyalkenyl compounds are the trivinylcyclohexanes, trivinylbenzenes, tetravinylcyclobutane, trivinyltrimethylcyclotrisiloxane, tetramethyltetravinylcyclotetrasiloxane, triallylcyanurate, and triallylisocyanurate. Trivinylcyclohexanes are preferred.

The silyl hydride employed in the hydrosilylation reaction is not particularly limited. It can be any compound selected from the group consisting of $R_aSiH_{4-a}$, $(RO)_aSiH_{4-a}$, $HSiR_a(OR)_{3-a}$, $Q_uT_vT_p^HD_wD^H_xM^H_yM_z$, $R_3Si(CH_2)_f(SiR_2O)_eSiR_2H$, $(RO)_3Si(CH_2)_f(SiR_2O)_eSiR_2H$ and combinations thereof. The silyl hydride can contain linear, branched or cyclic structures, or combinations thereof. As used herein, each occurrence of R is independently C1-C18 alkyl, C1-C18 substituted alkyl, aryl, or substituted aryl, wherein R optionally contains at least one heteroatom, each occurrence of a independently has a value from 1 to 3, f has a value of 1 to 8, e has a value of 1 to 11, each of p, u, v, y and z independently has a value from 0 to 20, w and x are from 0 to 1000, provided that p+x+y equals 1 to 3000 and the valences of the all the elements in the silyl hydride are satisfied. Preferably, f is from 2 to 4, e is from 1 to 3, p, u, v, y, and z are from 0 to 10, w and x are from 0 to 100, wherein p+x+y equals 1 to 100.

As used herein, an "M" group represents a monofunctional group of formula $R'_3SiO_{1/2}$, a "D" group represents a difunctional group of formula $R'_2SiO_{2/2}$, a "T" group represents a trifunctional group of formula $R'SiO_{3/2}$, and a "Q" group represents a tetrafunctional group of formula $SiO_{4/2}$, an "$M^H$" group represents $H_gR'_{3-g}SiO_{1/2}$, a "$T^H$" represents $HSiO_{3/2}$, and a "$D^H$" group represents $R'HSiO_{2/2}$. As used herein, g is an integer from 0 to 3. Each occurrence of R' is independently C1-C18 alkyl, C1-C18 substituted alkyl, aryl or substituted aryl, wherein R' optionally contains at least one heteroatom.

In some embodiments, suitable silyl hydride affording selective mono-hydrosilylation of polyunsaturated compounds has one of the following structures: $R^3_3SiH$ (Formula VI), $HSi(OR^4)_3$ (Formula VII),

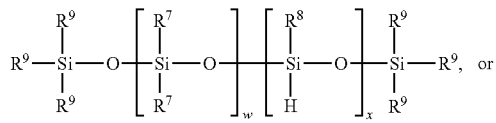

(Formula VIII)

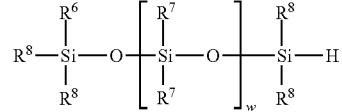

(Formula IX)

wherein each occurrence of $R^3$, $R^4$, $R^7$, $R^8$, and $R^9$ is independently a C1-C20 alkyl or an aryl group; $R^6$ is hydrogen, a C1-C20 alkyl or an aryl group; and w and x are independently greater than or equal to 0. In one embodiment, each occurrence of $R^3$, $R^4$, $R^6$, $R^7$, $R^8$, and $R^9$ is independently a C1-C5 alkyl or a benzyl group.

Exemplary silyl hydrides suitable for the present invention include, but are not limited to, trialkylsilanes like $(C_2H_5)_3SiH$, trialkoxysilanes like $(CH_3O)_3SiH$ and $(C_2H_5O)_3SiH$, hydridodisiloxanes like $(CH_3)_3SiOSi(CH_3)_2H$, hydridotrisiloxanes like $[(CH_3)_3SiO]_2SiH(CH_3)$, and hydridocyclosiloxanes like $[(CH_3)_2SiO]_3OSiH(CH_3)$ and $[(CH_3)_2SiO]_4OSiH(CH_3)$.

The catalysts suitable for the process of the invention is a complex of the Formulae (I), (II), or (III) as illustrated above. In connection with these formulae, G can be Mn, Fe, Ni, or Co in all the valence states. Advantageously G is iron or cobalt. More advantageously M is Fe, such as Fe (II) and Fe (III).

As used in the instant application, "alkyl" includes straight, branched and cyclic alkyl groups. Specific and non-limiting examples of alkyls include, but are not limited to, methyl, ethyl, propyl and isobutyl. In some embodiments, the alkyl group is a C1-C10 alkyl. In other embodiments, it is a C1-C6 alkyl.

By "substituted alkyl" herein is meant an alkyl group that contains one or more substituent groups that are inert under the process conditions to which the compound containing these groups is subjected. The substituent groups also do not substantially interfere with the hydrosilylation processes described herein. In some embodiments, the substituted alkyl group is a C1-C10 substituted alkyl. In other embodiments, it is a C1-C6 substituted alkyl. The substituents for the alkyl include, but are not limited to, the inert functional groups described herein.

By "aryl" herein is meant a non-limiting group of any aromatic hydrocarbon from which one hydrogen atom has been removed. An aryl may have one or more aromatic rings, which may be fused, connected by single bonds or other groups. Specific and non-limiting examples of aryls include, but are not limited to, tolyl, xylyl, phenyl, and naphthalenyl.

By "substituted aryl" herein is meant an aromatic group that contains one or more substituent groups that are inert under the process conditions to which the compound containing these substituent groups is subjected. The substituent groups also do not substantially interfere with the hydrosilylation processes described herein. Similar to an aryl, a substituted aryl may have one or more aromatic rings, which may be fused, connected by single bonds or other groups; however, when the substituted aryl has a heteroaromatic ring, the free valence in the substituted aryl group can be to a heteroatom (such as nitrogen) of the heteroaromatic ring instead of a carbon. If not otherwise stated, it is preferred that the substituents of the substituted aryl groups herein contain 0 to about 30 carbon atoms, specifically from 0 to 20 carbon atoms, more specifically, from 0 to 10 carbon atoms. In one embodiment, the substituents are the inert groups described herein.

By "alkenyl" herein is meant any straight, branched, or cyclic alkenyl group containing one or more carbon-carbon double bonds, where the point of substitution can be either at a carbon-carbon double bond or elsewhere in the group. Specific and non-limiting examples of alkenyls include, but are not limited to, vinyl, propenyl, allyl, methallyl, and ethylidenyl norbornane.

By "alkynyl" is meant any straight, branched, or cyclic alkynyl group containing one or more carbon-carbon triple bonds, where the point of substitution can be either at a carbon-carbon triple bond or elsewhere in the group.

By "unsaturated" is meant one or more double or triple bonds. In a preferred embodiment, it refers to carbon-carbon double or triple bonds.

By "inert functional group" herein is meant a group other than hydrocarbyl or substituted hydrocarbyl which is inert under the process conditions to which the compound containing the group is subjected. The inert functional groups also do not substantially interfere with any hydrosilylation processes described herein. Examples of inert functional groups include halo (fluoro, chloro, bromo, and iodo), ether such as —$OR^{30}$ wherein $R^{30}$ is hydrocarbyl or substituted hydrocarbyl.

"Heteroatom" herein is meant any of the Group 13-17 elements except carbon, and can include for example oxygen, nitrogen, silicon, sulfur, phosphorus, fluorine, chlorine, bromine, and iodine.

In some embodiments, the complexes disclosed herein include those of Formulae (I) and (II) having the following substituents: (1) $R_{23}$ is

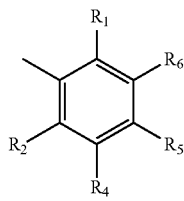

and/or (2) $R_1$ is hydrogen, methyl, ethyl, n-propyl or isopropyl; and/or (3) $R_1$ and $R_2$ are both methyl, ethyl, n-propyl or isopropyl groups; and/or (4) $R_3$ is methyl; and/or (5) $R_4$ to $R_9$ are hydrogen; and/or (6) $R_{10}$, $R_{11}$, $R_{13}$, $R_{14}$, $R_{15}$, and $R_{16}$ are hydrogen; and/or (7) $R_{22}$ is —$CH_2SiR^{20}_3$, wherein each occurrence of $R^{20}$ is C1-C18 alkyl, C1-C18 substituted alkyl, aryl or substituted aryl, preferably $R^{20}$ is a methyl or ethyl group.

In connection with Formula (II), $L_1$-$L_2$ typically contains at least two unsaturated sites per molecule. Further examples of $L_1$-$L_2$ include, but are not limited to, butadienes, 1,5-cyclooctadienes, dicyclopentadienes, norbornadienes, trivinylcyclohexane, tetramethyltetravinylcyclotetrasiloxane, and divinyl tetramethyl disiloxane.

In some embodiments, $L_1$-$L_2$ contains at least four unsaturated sites per molecule. In this circumstance, it is possible to form a metal-PDI dimer (PDI-metal-$L_1$-$L_2$-metal-PDI) with each metal bonding to two unsaturated sites of $L_1$-$L_2$. Exemplary $L_1$-$L_2$ for the metal-PDI dimer is tetravinyltetramethylcyclotetrasiloxane.

In connection with Formula (III), In one embodiment, $R_6$ is aryl or substituted aryl, and $R_1$ to $R_5$, $R_7$ to $R_9$, $R_{19}$, and $R_{20}$ are hydrogen. In another embodiment, $R_1$ to $R_9$, $R_{19}$ and $R_{20}$ are hydrogen.

Also in Formula (III), in one embodiment, X is covalently bonded to G through a carbon atom. In another embodiment, X does not contain beta hydrogen. Typically, the alpha carbon refers to the carbon that attaches to G. By extension, the beta carbon refers to the carbon that attaches to the alpha carbon.

As used herein, beta-hydrogen is meant the hydrogen attached to the beta carbon. Preferably, each X is independently a moiety represented by —$CH_2SiR^{20}_3$, wherein each occurrence of $R^{20}$ is C1-C18, preferably C1-C10, more preferably C1-C6 alkyl, C1-C18, preferably C1-C10, more preferably C1-C6 substituted alkyl, aryl or substituted aryl. In some embodiments, $R^{20}$ is a methyl or an ethyl group.

When used as catalysts for the hydrosilylation reactions, the complexes of Formulae (I), (II), and (III) can be unsupported or immobilized on a support material, for example, carbon, silica, alumina, $MgCl_2$ or zirconia, or on a polymer or prepolymer, for example polyethylene, polypropylene, polystyrene, or poly(aminostyrene). The metal complexes can also be supported on dendrimers.

In some embodiments, for the purposes of attaching the metal complexes of the invention to a support, it is desirable that at least one of $R_1$ to $R_9$ of the metal complexes of Formulae (I), (II) and (III), preferably $R_6$, has a functional group that is effective to covalently bond to the support. Exemplary functional groups include but are not limited to SH, COOH, $NH_2$ or OH groups.

In certain embodiments, silica supported catalyst may be prepared via Ring-Opening Metathesis Polymerization (ROMP) technology as discussed in the literature, for example Macromol. Chem, Phys, 2001, 202, No. 5, pages 645-653; Journal of Chromatography A, 1025 (2003) 65-71, the content of which is incorporated herein by reference in its entirety.

Another way to immobilize catalysts on the surface of dendrimers is by the reaction of Si—Cl bonded parent dendrimers and functionalized complexes of Formulae (I), (II) and (III) in the presence of a base as illustrated by Kim et al. in Journal of Organometallic Chemistry 673 (2003) 77-83, the content of which is incorporated herein by reference in its entirety.

In the composition to be reacted for the formation of the mono-hydrosilylated product, the molar ratio of Si—H functional groups in the silyl hydride to the alkenyl functional groups in the polyunsaturated compound is between about (0.5/α) and about (1.1/α), where a is an integer from 2 to 6. If the ratio is lower than about (0.5/α), the reaction would end up with large quantities of unreacted polyunsaturated compound. If the ratio is greater than about (1.1/α), the reaction would produce excessive bis-hydrosilylation products, thus resulting in reduced selectivity. Preferably, the ratio is about (1/α). Selective towards mono-hydrosilylation is favored by slow addition of the silyl hydride to the reaction mixture comprising the polyunsaturated compound and the non-precious metal-based catalyst as described above.

The amount of catalyst in the reaction mixture calculated based on the non-precious metal catalyst in the total mass of the reaction mixture is 1-10,000 parts per million (ppm), specifically 10-5000 ppm, more specifically 20-2000 ppm.

The temperature of the reaction leading to selective mono-hydrosilylation can be from about −50° C. to about 120° C., specifically from 0° C. to 80° C. and, more specifically, from 10° C. to 60° C. Since the hydrosilylation is exothermic, it might be necessary to apply cooling to control the temperature with narrow limits, depending on the particular polyunsaturated compound and silyl hydride used.

Solvents aid in the dissolution of the catalysts as well as in the control of reaction rate. Hydrocarbon solvents such as toluene and pentane are suitable. Selective mono-hydrosilylation is favored by dissolving the silyl hydride in the solvent and adding the solution slowly to the reaction mixture comprising the polyunsaturated compound and the catalyst of the invention. An effective rate of addition is that which minimizes both the reaction exotherm and the extent of bis-hydrosilylation.

In another embodiment, the present invention is directed to the composition produced from the process described above. In the composition, the ratio of the mono-hydrosilylated product to the bis-hydrosilylated product is greater than about 1.8, specifically greater than about 3, more specifically greater than about 4.

Another preferred embodiment is the composition produced by the monohydrosilylation of trivinylcyclohexane. The composition contains a monosilylated divinylcyclohexane product having one of the following general formulae:

(H₂C=CH)₂C₆H₉CH₂CH₂—Si(OR)₃    FORMULA X:

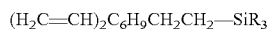
(H₂C=CH)₂C₆H₉CH₂CH₂—SiR₃    FORMULA XI:

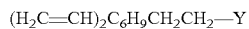
(H₂C=CH)₂C₆H₉CH₂CH₂—Y    FORMULA XII:

In Formulae X and XI, R represents branched or straight-chained C1-C20 alkyl, C3-C20 cycloalphatic or aromatic groups. The groups are not necessarily all the same in a single molecule. Thus, in Formula XI, one R group can be octyl, another methyl and the third tert-butyl. R is methyl, ethyl or isopropyl in the preferred compounds of Formula X and Formula XI.

In Formula XII, Y is a univalent siloxanyl radical of general Formula (XIII), (XIV) or (XV) in which R represents branched or straight-chained alkyl, cycloalphatic or aromatic groups of 1 to 20 carbon atoms, and x is greater than or equal to zero.

FORMULA XIII: R₃SiO(SiR₂O)ₓ(RSiO)SiR₃
FORMULA XIV: R₃SiO(SiR₂O)ₓSiR₂—
FORMULA XV: (R₂SiO)ₓOSiR

Examples of mono-hydrosilylated compounds of Formula XII are

(H₂C=CH)₂C₆H₉CH₂CH₂—Si[OSi(CH₃)₃]₂CH₃

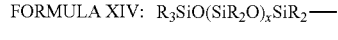
(H₂C=CH)₂C₆H₉CH₂CH₂—Si(CH₃)₂—O—Si
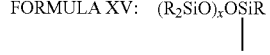
(CH₃)₂CH₂CH₂Si(CH₃)₃.

Commercial trivinylcyclohexane occurs primarily as mixtures of stereoisomers with vinyl groups at the 1, 2 and 4 positions. However, stereoisomers with 1,2,3- and 1,3,5-vinyl substitution are also known. The following specifications are based on the 1,2,4-isomeric mixture, but they are also generally applicable to the other two trisubstituted isomeric mixtures.

In the 1,2,4-trivinylcyclohexane stereoisomers, the differences are in the orientation of the vinyl groups relative to each other (cis versus trans), and relative to the cyclohexane ring (equatorial versus axial). This results in a total of eight stereoisomers, which occur as four mirror-image pairs of enantiomers. These four pairs, each being diastereomers of each other, can be separated from each other in the mixture by careful distillation. No separation by distillation occurs between the enantiomers of each pair. Thus, four compositions can be obtained, each being a racemic mixture of two mirror-image enantiomers. These four compositions will be referred to herein as Isomer A, Isomer B, Isomer C, and Isomer D, respectively. Their designations as A, B, C, or D are based on the order in which they are collected using a multiplate distillation column, A being the first, and D the last.

Despite the ability to separate Isomers A, B, C, and D in principle, this is not trivial in practice. The boiling points of all four fall within a very narrow temperature range: about 3° C. or less. Moreover, two pairs, Isomers A and B, and Isomers C and D, boil within well under 1° C. of each other. Separating even just two components within this narrow boiling range requires good columns and tight process control. The occurrence of not two, but four components makes the separations substantially more challenging. Additional complications arise because the available commercial trivinylcyclohexane mixtures further contain a plethora of other impurities, the vast majority of them having boiling points close to that of the trivinylcyclohexane. The impurities consist of both lower boilers than trivinylcyclohexane and higher boilers.

Figure 1: Four Isomeric Forms (A, B, C & D) of 1,2,4-Trivinylcyclohexane

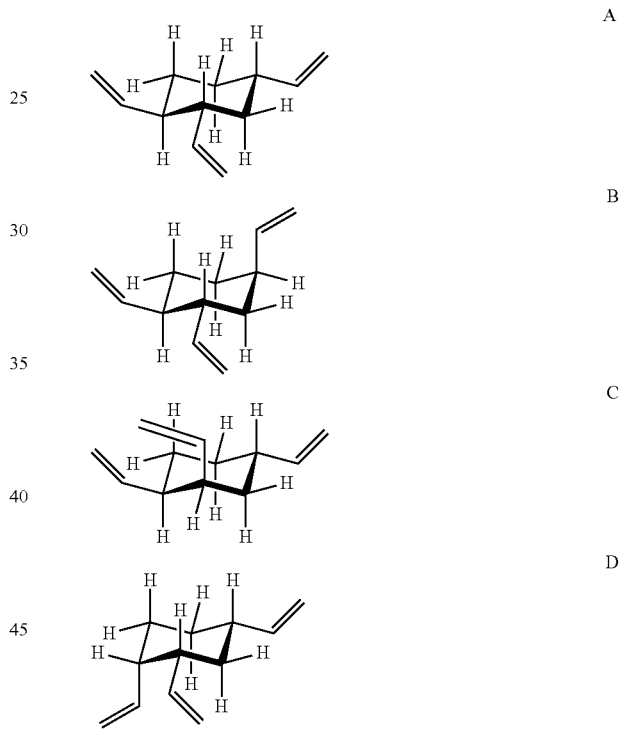

Two-dimensional NMR correlation spectroscopy (COSY) has been used to assign the orientation of the vinyl groups in the Isomer A, B, C and D distillation fractions. The vinyl groups in Isomer A are all equatorial, while in Isomer B, only those at positions 1 and 2 are equatorial, and that at position 4 is axial. In Isomer C, the vinyl group at position 2 is axial and those at positions 1 and 4 are equatorial. In Isomer D, the axial vinyl group is at position 1; the equatorial vinyl groups are positions 2 and 4. The structures of Isomers A, B, C and D are shown in Figure 1. These different structures determine the reactivity of the trivinylcyclohexane stereoisomers and the selectivity to mono-hydrosilylation products.

When hydrosilylation of the undistilled mixture of trivinylcyclohexane stereoisomers, or of the individual distillation fractions labeled Isomer A and B is catalyzed with the catalysts of the invention, for example iron pyridinediimine catalysts, the initial addition of the silyl group occurs preferentially at the 4 position of the cyclohexane ring. This preference is significantly higher for the stereoisomers in the A fraction. Accordingly, not only is selective mono-hydrosilylation realized, but also regioselective mono-hydrosilylation at the 4 position. In contrast, platinum-catalyzed hydrosilylation of trivinylcyclohexane results in near random addition of the silyl functionality to the vinyl groups with no particular preference for the 1, 2 or 4 position.

The regioselective, non-precious metal complex (for example iron pyridinediimine)-catalyzed mono-hydrosilylation allows the selective synthesis of 1,2-divinyl,4-(2-triethoxysilyl-ethyl)cyclohexane in at least 65 weight percent yield, preferably in at least 75 weight percent yield, from Isomer A and triethoxysilane. The gravimetric ratio of mono-hydrosilylated product to the bis-hydrosilylated product is greater than 2, preferably greater than 4 and most preferably greater than 6. As was stated hereinabove, 1,2-divinyl,4-(2-triethoxysilylethyl)cyclohexane is a key intermediate in the synthesis of sulfur silanes useful for improving rolling resistance and wear in automobile tires. Accordingly, the present invention provides a useful way to selectively prepare this important intermediate.

Likewise, 1,2-divinyl, 4-(2-heptamethyltrisiloxanyl)cyclohexane, useful for forming homo and copolymer films, is obtained regioselectively from the reaction of Isomer A and/or Isomer B with bis(trimethylsiloxy)methylsilane catalyzed by the catalysts of the invention, for example iron pyridinediimine complexes. The gravimetric ratio of mono-hydrosilylated product to the bis-hydrosilylated product is greater than 3, preferably greater than 4 and most preferably greater than 6.

Accordingly, in one embodiment, the present invention relates to a process for selectively producing a mono-hydrosilylated product from trivinylcyclohexane and a silyl hydride comprising reacting trivinylcyclohexane with the silyl hydride in the presence of a complex of Formula (I), Formula (II) or Formula (III) described above, wherein the molar ratio of the Si—H functional groups in the silyl hydride to the alkenyl functional groups in the trivinylcyclohexane is between about (0.5:3) and about (1.1:3); and wherein the silyl group from the silyl hydride is selectively added to the 4 position of trivinylcyclohexane.

In connection with the process, the silyl hydride can be triethoxysilane or bis(trimethylsiloxy)methylsilane. The trivinylcyclohexane can be a mixture of trivinylcyclohexane stereoisomers or trivinylcyclohexane isomer A and/or trivinylcyclohexane isomer B.

Although the present invention is described mainly in the context of mono-hydrosilylation, it is appreciated that advantageously, the catalysts of the invention are effective to produce regioselective bis-hydrosilylated products from a substrate containing at least three unsaturated groups.

Illustratively, for Isomer C of 1,2,4-trivinylcyclohexane, mono-hydrosilylation occurs at either of the equatorial vinyl groups at positions 1 and 4 of the cyclohexane ring, and bis-hydrosilylation occurs almost exclusively at 1 and 4 positions of the cyclohexane ring. Thus, with Isomer C, regioselective bis-hydrosilylation is realized. Isomer D of 1,2,4-trivinylcyclohexane also shows a preference for regioselective bis-hydrosilylation. For Isomer D, the addition occurs at the vinyl groups attached to positions 2 and 4 of the cyclohexane ring.

The following examples are intended to illustrate, but in no way limit the scope of the present invention. All parts and percentages are by weight and all temperatures are in degrees Celsius unless explicitly stated otherwise.

EXAMPLES

General Considerations

All air- and moisture-sensitive manipulations were carried out using standard vacuum line, Schlenk, and cannula techniques or in an MBraun inert atmosphere drybox containing an atmosphere of purified nitrogen. Solvents for air- and moisture-sensitive manipulations were initially dried and deoxygenated using literature procedures. See for example Pangborn et al., J. Organometallics 1996, 15, 1518.

$[(^{2,6-Et2}PDI)Fe(N_2)]_2[\mu-(N_2)]$ corresponds to compound of Formula ((I) wherein all $R_{23}$ are 2,4-diethylphenyl, all $R_3$ are methyl, all $R_1$ and $R_2$ are ethyl, all $R_4$, $R_5$, $R_6$, $R_7$, $R_8$, $R_9$ are hydrogen, and G is Fe.

$[(^{2,6-Me2}PDI)Fe(N_2)]_2[\mu-(N_2)]$ corresponds to compound of Formula ((I) wherein all $R_{23}$ are 2,6-dimethylphenyl, all $R_1$, $R_2$ and $R_3$ are methyl, all $R_4$, $R_5$, $R_6$, $R_7$, $R_8$, $R_9$ are hydrogen, and G is Fe.

$[(^{2-Me,6-iPr}PDI)Fe(N_2)]_2[\mu-(N_2)]$ corresponds to compound of Formula ((I) wherein all $R_{23}$ are 2-methyl-6-isopropylphenyl, all $R_1$ and $R_3$ are methyl, all $R_2$ are isopropyl, all $R_4$, $R_5$, $R_6$, $R_7$, $R_8$, $R_9$ are hydrogen, and G is Fe.

$[^{2,4,6-Me3}PDIFe(N_2)]_2[(\mu-N_2)]$ corresponds to compound of Formula ((I) wherein all $R_{23}$ are 2,4,6-trimethylphenyl, all $R_1$, $R_2$, $R_3$ and $R_5$ are methyl, all $R_4$, $R_6$, $R_7$, $R_8$, $R_9$ are hydrogen, and G is Fe.

Example 1

Separation of Commercial Trivinyleyclohexane (TVCH)

This Example illustrates the separation of commercial trivinylcyclohexane (TVCH) into fractions corresponding to Isomers A, B, C and D, as defined hereinabove, and the characterization of the fractions by gas chromatography (GC) and NMR spectroscopy.

Distillation Apparatus

A batch distillation apparatus was set up to separate the TVCH isomers. The apparatus comprised a 5-liter flask as a boiler, which was fitted to a 50 mm diameter vacuum-jacketed distillation column filled with 316 stainless steel protruded metal packing (Propac; 0.16 inch size; H.S. Martin, Inc. item number 509100-0016) to a height of 1700 mm. The bottom of the column had a drip tip to permit the determination of the reflux return rate by visually monitoring the rate at which liquid dripped back into the boiler. The top of the column was fitted with an adjustable distillate takeoff head. Heat was supplied to the flask by an electric heating mantle (Glas Col). Power was supplied to the heating mantle by a variable voltage controller (Staco, Dayton, Ohio). Agitation was supplied to the boiler by a teflon-coated magnetic stir bar, powered by an electric stir plate, which supported the heating mantle containing the boiler.

Distillation Procedure

The boiler was typically charged with 4700 to 4800 mL of TVCH and 4 grams of tert-butylcatechol as a polymerization inhibitor. The distillation was carried out with an absolute head pressure of 9 torr (~1200 Pa). Electric power to the heating mantle was adjusted to establish and maintain a boilup ratio of about 1 liter per 2 hours, which was measured at, and monitored at 6 drops of reflux return per second. This resulted in a boiling point in the range of 86-88° C.

A reflux/takeoff ratio of 20-25 was maintained. The first 100 mL of distillate contained a concentrate of lower boiling impurities and was discarded. Additional fractions of distillate were then collected and stored in separate vessels. Several batches were distilled in this way to accumulate enough of each fraction to run a full batch for redistillation. After multiple redistillations, Isomers A and B were eventually obtained at acceptable purity levels. Isomers C and D were obtained as mixtures with variable C/D ratios, virtually free of Isomers A and B.

Analysis of Isomer Components

The TVCH fractions were analyzed by gas chromatography (GC). GC runs were carried out with an Agilent 6890 column. The column was an HP-5 (5% phenyl, 95% methylpolysiloxane), with a length of 30 meters. The column inner diameter was 0.25 mm., and the film thickness was 250 μm. The carrier gas was helium with a 100/1 split ratio. The injection port and GC detector temperatures were 250° C. and 350° C., respectively. Injection volume was 1 μl. The oven temperature was held at 50° C. for 2 minutes before it was raised at a rate of 8° C. per minute to 340° C., and then held at that temperature for 6 minutes. Three closely spaced, but well separated GC peaks were obtained in the chromatograms. Isomers A and B eluted in the same order as in the distillation. Isomers C and D eluted last, as a single, completely unresolved peak. C-13 NMR was used to determine the ratios of Isomers C and D. C-13 NMR resonances of the cyclohexyl ring carbons occur at characteristic chemical shifts in Isomers C and D. The intensities of the resonances can be used to determine the molar ratio of Isomer C to Isomer D in the distillate. Characteristic C-13 NMR chemical shifts of Isomer C are at 26,67, 32.44, 41.60, 42.38, and 44.15 ppm. Characteristic C-13 NMR chemical shifts of Isomer D are at 26.24, 35.58, 37.79, 42.82 and 44.04 ppm.

Two-dimensional proton NMR correlation spectroscopy (COSY) was used to assign the orientation of the vinyl groups in the four fractions. All three vinyl groups are equatorial in Isomer A. In Isomer B, the vinyl group at position 4 is axial and those at positions 1 and 2 are equatorial. In Isomer C, the axial vinyl group is at position 2 and in Isomer D at position 1.

Example 2

Selective Mono-Hydrosilylation of TVCH Isomer A by bis(Trimethylsiloxy)Methylsilane ($MD^HM$)

The 1,2,4-trivinylcyclohexane sample used in this experiment was prepared as described in Example 1. It contained 98.4% Isomer A and 1.6% Isomer B. The experiment was conducted in an inert atmosphere.

A scintillation vial was charged with 1.0 g (6.16 mmol) 1,2,4-trivinylcyclohexane and 0.002 g (0.002 mmol) of $[(^{2,6-Et2}PDI)Fe(N_2)]_2[\mu-(N_2)]$ (0.03 mol % catalyst to silane). To the stirring solution was added 1.370 g (6.16 mmol) of $MD^HM$ dropwise over the course of 10 minutes at 23° C. The SiH/Vinyl molar ratio was (1:3). The reaction was stirred for 20 minutes and then quenched in air and analyzed by GC. The major GC peak was the mono-hydrosilylated product, which was 76.9% of the total mass. The bis-hydrosilylated product was 17.6%. Thus, the gravimetric ratio was 4.4.

Proton NMR showed that 90% of the mono-hydrosilylation product was the regioisomer in which silylation had occurred in the vinyl group at the 4 position of the cyclohexane ring. The crude product was distilled under fill vacuum, yielding a >90% pure mono-hydrosilylation product that was 90% the 4-substituted regioisomer. This isomer, 1,2-divinyl, 4-(2-heptamethyltri-siloxanyl)cyclohexane, had the following proton NMR parameters. $^1H$ NMR: δ=5.65-5.74 (m, 2H, $C_1HCHCH_2$ and $C_2HCHCH_2$), 4.95-5.04 (m, 2H, $C_1HCHC\underline{H}_2$ and $C_2HCHC\underline{H}_2$), 1.84 (ddd, 1H, J=13 Hz, 3 Hz, 2 Hz, $C_3H_{ax}\underline{H}_{eq}$), 1.72-1.79 (m, 2H, $C_5H_{ax}\underline{H}_{eq}$ and $C_6H_{ax}\underline{H}_{eq}$), 1.65 (m, 1H, $C_1\underline{H}CHCH_2$), 1.37 (m, 2H, $C_4HC\underline{H}_2CH_2Si$), 1.11-1.21 (in, 2H, $C_4\underline{H}_{ax}$ and $C_6\underline{H}_{ax}H_{eq}$), 0.76-0.88 (n, 2H, $C_3\underline{H}_{ax}H_{eq}$ and $C_5\underline{H}_{ax}H_{eq}$), 0.60 (m, 2H, $C_4HCH_2C\underline{H}_2Si$), 0.19 (s, 18H, $SiM\underline{e}_3$), 0.16 (s, 3H, $SiM\underline{e}$). $^{13}C$ NMR: 143.89, 143.85, 114.04, 113.93, 47.81, 47.76, 40.36, 39.82, 33.31, 32.77, 31.34, 15.44, 2.43, 0.32.

Example 3

Mono-Hydrosilylation of TVCH Isomer A with Triethoxysilane (TES)

The 1,2,4-trivinylcyclohexane sample used in this experiment was prepared as described in Example 1. It contained 98.4% Isomer A and 1.6% Isomer B. TES was prepared by the Direct Process disclosed in U.S. Pat. No. 7,429,672.

In an inert atmosphere at 23° C., a scintillation vial was charged with 0.150 g (0.92 mmol) of 1,2,4-trivinylcyclohexane and 0.150 g (0.92 mmol) of TES. The SiH/Vinyl molar ratio was (1:3). To the stirring solution was added 0.002 g (0.002 mmol) of $[(^{2,6-Et2}PDI)Fe(N_2)]_2[\mu-(N_2)]$ (0.2 mol % catalyst to silane). An exotherm occurred. The reaction was stirred for about 60 minutes and then quenched in air. Analysis of the reaction mixture by GC and GC/MS provided evidence that TES was completely consumed and that the mono and bis-hydrosilylation products were present in 60.2% and 24.4%, respectively. The gravimetric ratio was 2.46.

Proton NMR analysis revealed that mono-hydrosilylation had occurred with 90% regioselectivity at the vinyl group at position 4 of the cyclohexane ring.

Examples 4A, 4B

Selective Mono-Hydrosilylation of TVCH by $MD^HM$ with $[(^{2-Me,6-iPr}PDI)Fe(N_2)]_2[\mu-(N_2)]$ Distilled TVCH of the same composition (98.4% Isomer A and 1.6% Isomer B) used in Example 3 was also used in Example 4A. Distilled TVCH used in Example 4B contained 47% Isomer A and 53% Isomer B.

The experiments of this Example were performed by mixing 1.0 g 1,2,4-trivinyl-cyclohexane, 1.37 g $MD^HM$ in a scintillation vial according to the procedure of Example 3. The SiH/Vinyl molar ratio was (1:3). 0.002 g catalyst was then added. There was an exotherm. Complete consumption of SiH functional groups occurred within 10 minutes at 23° C. GC analytical data are summarized in the table below.

| | EXAMPLE 4A | EXAMPLE 4B |
|---|---|---|
| CATALYST | $[(^{2-Me,6-iPr}PDI)Fe(N_2)]_2[\mu-(N_2)]$ | $[(^{2-Me,6-iPr}PDI)Fe(N_2)]_2[\mu-(N_2)]$ |
| TVCH | 98.4% Isomer A | 47% Isomer A |
| | 1.6% Isomer B | 53% Isomer B |
| Mono PRODUCT | 74.0 | 61.3 |
| Bis PRODUCT | 17.2 | 27.3 |
| RATIO | 4.30 | 2.25 |

Proton NMR analysis showed that 90-95% of the mono-hydrosilylation product from both experiments was 1,2-divinyl, 4-(2-heptamethyltrisiloxanyl)cyclohexane, in which MD$^H$M addition had occurred regioselectively at the vinyl group at position 4 of the cyclohexane ring. The results confirm that [($^{2-Me,6-iPr}$PDI)Fe(N$_2$)]$_2$[μ-(N$_2$)] is an effective catalyst for the room temperature regioselective mono-hydrosilylation of polyalkenyl substrates.

Example 5

This Example compares the hydrosilylation performance of the iron pyridinediimine catalysts of this invention with the conventional platinum catalysts. Commercial TVCH containing all four diastereomers was used in the experiments of this example.

Example 5A

Comparative Experiment with Karstedt's Pt Catalyst (2-Triethoxysilylethyl)divinylcyclohexane was prepared from triethoxysilane and 1,2,4-trivinylcyclohexane using the procedure disclosed in Example 1 of U.S. Pat. No. 7,696,269 for trimethoxysilane and 1,2,4-trivinylcyclohexane. A 5 liter, three-neck round bottomed flask fitted with a heating mantle, mechanical stirrer, addition funnel, Friedrich condenser, nitrogen inlet and thermocouple/temperature controller was charged with 1800 g TVCH (11.1 moles) and 3.6 g of a solution (1 wt % Pt) of Karstedt's platinum catalyst in xylene. The contents of the flask were stirred and heated to 90° C. Triethoxysilane (1641 g, 9.99 moles), which had been placed in the addition funnel, was then added slowly over a four hour period to control the exotherm. The temperature remained between 101-109° C. during the addition. The SiH/Vinyl molar ratio in the reaction was 1:3. GC analysis of the crude reaction product gave 21 wt % unreacted TVCH, 48 wt % mono-hydrosilylated product, ((2-Triethoxysilylethyl)divinylcyclohexane), 26.3 wt % bis ((2-Triethoxysilylethyl)vinylcyclohexane and 2.7 wt % tris ((2-Triethoxysilylethyl) cyclohexane. The gravimetric ratio of mono to bis was 1.82.

GC of the reaction product from this platinum catalyzed TVCH hydrosilylation showed three closely-spaced peaks of near equal intensity eluting with retention times corresponding to the mono-hydrosilylated product. This is in contrast to the reaction products obtained with the iron pyridinediimine catalysts. Typically, one peak, corresponding to the regioisomer with silylation of the vinyl group at position 4 of the cyclohexane ring, dominates this retention time portion of the gas chromatogram. Accordingly, it can be concluded that platinum catalysis allows hydrosilylation of the three vinyl groups with near equal probability. Thus, platinum catalysis does not confer the regioselectivity realized with the iron pyridinediimine catalysts.

Example 5B

Experiment with [($^{2,6-Et2}$PDI)Fe(N$_2$)]$_2$[μ-(N$_2$)] and Commercial TVCH

This experiment was performed as described in Example 3. Reaction was complete in 15 minutes at 23° C. The complete consumption of triethoxysilane was confirmed both with GC and proton NMR. GC analysis revealed 63% mono-hydrosilylated product and 23% bis-hydrosilylated product. The gravimetric ratio was 2.74. Proton NMR showed that ~95% of the mono-hydrosilylated product had been silylated at the vinyl group in the 4 position on the cyclohexane ring. Thus, catalysis with [($^{2,6-Et2}$PDI)Fe(N$_2$)]$_2$[μ-(N$_2$)] afforded both chemical selectivity and regioselectivity.

Example 5C

Experiment with [($^{2,6-Me2}$PDI)(Fe(N$_2$)]$_2$[μ-(N$_2$)] and commercial TVCH This experiment was performed as described in Example 3. Reaction was complete in 15 minutes at 23° C. The complete consumption of triethoxysilane was confirmed both with GC and proton NMR. GC analysis revealed 66% mono-hydrosilylated product and 16% bis-hydrosilylated product. The gravimetric ratio was 4.13. Proton NMR showed that ~90% of the mono-hydrosilylated product had been silylated at the vinyl group in the 4 position on the cyclohexane ring. Thus, catalysis with [($^{2,6-Me2}$PDI)Fe(N$_2$)]$_2$[μ-(N$_2$)] afforded both chemical selectivity and regioselectivity.

Example 6

Hydrosilylation of 1,2,4-Trivinylcyclohexane with Triethylsilane

In an inert atmosphere, a scintillation vial was charged with 0.150 g (0.92 mmol) of 1,2,4-trivinylcyclohexane and 0.107 g (0.92 mmol, 0.99 eq.) of triethylsilane. To the stirring solution was added 0.002 g (0.002 mmol) of [($^{2,6-Me2}$PDI)Fe(N$_2$)]$_2$[μ-(N$_2$)] (0.5 mol % to silane). The reaction was stirred for typically 60 minutes and the reaction was quenched in air and analyzed by GC. The GC indicated a majority (~75%) of the single addition product, the majority of which occurred in the 4 position. $^1$H NMR: δ=5.90-5.77 (m, 2H, C$_1$HCHCH$_2$ and C$_2$HCHCH$_2$), 5.18-5.08 (m, 2H, C$_1$HCHCH$_2$ and C$_2$HCHCH$_2$), 2.01-1.74 (m, 6H), 1.38-1.06 (m, 11H), 0.98-0.85 (m, 1H), 0.74-0.95 (m, 8H) $^{13}$C: 143.97, 143.88, 114.06, 113.94, 47.86, 47.83, 40.89, 39.72, 33.30, 32.71, 31.96, 8.80, 8.17, 3.97.

Example 7

Hydrosilylation of TVCH with Methylbis(Trimethylsilyloxy)Silane (MD$^H$M) with [$^{2,4,6-Me3}$PDIFe(N$_2$)]$_2$[(μ-N$_2$)]

In an inert atmosphere, to a scintillation vial was added 0.100 g (0.614 mmol) of 1,2,4-trivinylcyclohexane (predominantly isomer A) and 0.136 g (0.614 mmol) of MD$^H$M and a stir bar. To this stirring solution was added 0.002 g of [$^{2,4,6-Me3}$PDIFe(N$_2$)]$_2$[(μ-N$_2$)] (1 mol % to silane). The reaction was allowed to stir for 15 minutes, at which time the solution was analyzed by GC. The GC trace indicated a distribution similar to that of [$^{2,6-Me2}$PDIFe(N$_2$)]$_2$[(μ-N$_2$)] and [$^{2,6-Et2}$PDIFe(N$_2$)]$_2$[(μ-N$_2$)], with 74% of the reaction solution mono-hydrosilylated product, predominantly at the C4 vinyl position.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A process for selectively producing a monosilylated product from a composition containing a silyl hydride and a polyunsaturated compound comprising contacting the composition with a complex of Formula (I), Formula (II) or Formula (III) to cause the silyl hydride to react with the polyunsaturated compound such that hydrosilylation occurs selectively at one unsaturated group of the unsaturated compound thereby producing the mono-hydrosilylated product, wherein the polyunsaturated compound is represented by Formula (IV) or Formula (V)

  (Formula IV)

  (Formula V)

wherein

E$^1$ is a divalent or polyvalent aliphatic or aromatic cyclic hydrocarbon group containing from 3 to 25 carbon atoms, or a divalent or polyvalent aliphatic or aromatic heterocyclic hydrocarbon containing from 3 to 25 carbon atoms, wherein the heteroatom is selected from the group consisting of oxygen, nitrogen, silicon and sulfur;

E$^2$ is a divalent or polyvalent cyclic silicone group containing from 3 to 8 silicon atoms and from 3 to 8 oxygen atoms;

each occurrence of R$^1$ and R$^2$ is independently a hydrogen or a hydrocarbon group containing from 1 to 8 carbon atoms; and each occurrence of α, β and γ is independently an integer, wherein α is 2 to 6; β is 0 to 6; and γ is 0 to 4;

wherein Formula (I), Formula (II) and Formula (III) are:

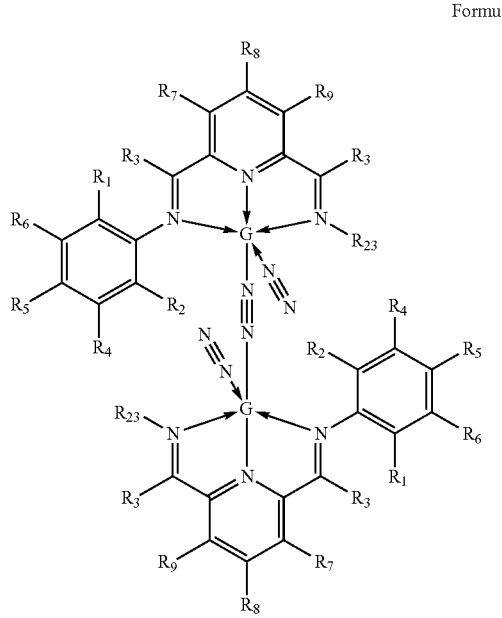
Formula (I)

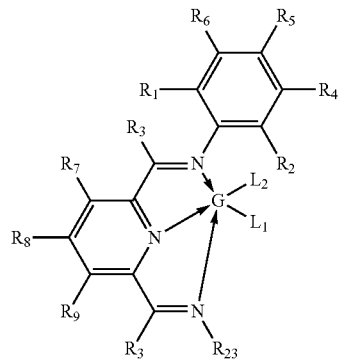
Formula (II)

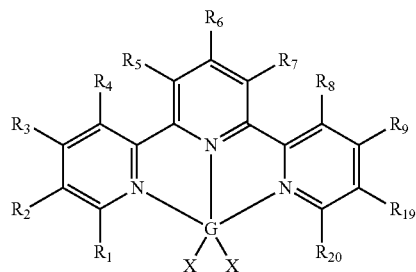
Formula (III)

wherein:

G is Mn, Fe, Ni, or Co;

each occurrence of R$_1$, R$_2$, R$_3$, R$_4$, R$_5$, R$_6$, R$_7$, R$_8$, R$_9$, R$_{19}$, and R$_{20}$ is independently hydrogen, C1-C18 alkyl, C1-C18 substituted alkyl, aryl, substituted aryl, or an inert functional group, wherein R$_1$ to R$_9$, R$_{19}$, R$_{20}$, other than hydrogen, optionally contain at least one heteroatom;

each occurrence R$_{23}$ is independently C1-C18 alkyl, C1-C18 substituted alkyl, aryl or substituted aryl, wherein R$_{23}$ optionally contains at least one heteroatom; and optionally any two of R$_1$, R$_2$, R$_3$, R$_4$, R$_5$, R$_6$, R$_7$, R$_8$, R$_9$, R$_{19}$, R$_{20}$, and R$_{23}$ vicinal to one another taken together may form a ring being a substituted or unsubstituted, saturated, or unsaturated cyclic structure;

each of L$_1$ and L$_2$ is independently C1-C18 alkyl, C1-C18 substituted alkyl, aryl, substituted aryl, C2-C18 alkenyl, C2-C18 alkynyl, or L$_1$-L$_2$ together is one of the following

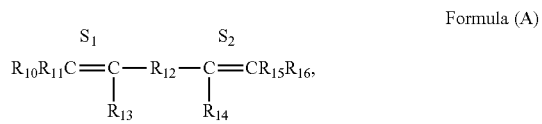
Formula (A)

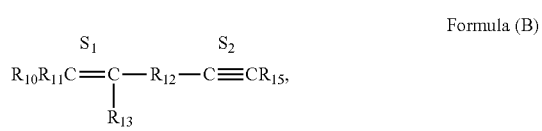
Formula (B)

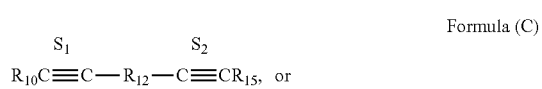
Formula (C)

-continued

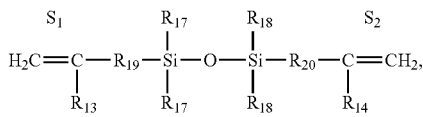
Formula (D)

wherein each occurrence of $R_{10}$, $R_{11}$, $R_{13}$, $R_{14}$, $R_{15}$ and $R_{16}$ is independently hydrogen, C1-C18 alkyl, C2-C18 alkenyl, or C2-C18 alkynyl, wherein $R_{10}$, $R_{11}$, $R_{13}$, $R_{14}$, $R_{15}$ and $R_{16}$, other than hydrogen, optionally contain at least one heteroatom, and $R_{10}$, $R_{11}$, $R_{13}$, $R_{14}$, $R_{15}$ and $R_{16}$, other than hydrogen, are optionally substituted;

each occurrence of $R_{12}$ is independently C1-C18 alkyl, C1-C18 substituted alkyl, C2-C18 alkenyl, C2-C18 substituted alkenyl, C2-C18 alkynyl, C2-C18 substituted alkynyl, aryl, substituted aryl, wherein $R_{12}$ optionally contains at least one heteroatom;

optionally any two of $R_{10}$, $R_{11}$, $R_{12}$, $R_{13}$, $R_{14}$, $R_{15}$, $R_{16}$ taken together may form a ring being a substituted or unsubstituted, saturated or unsaturated cyclic structure;

each occurrence of $R_{17}$ and $R_{18}$ is independently alkyl, substituted alkyl, aryl, or substituted aryl, wherein each of $R_{17}$ and $R_{18}$ optionally contains at least one heteroatom, and wherein $R_{17}$ and $R_{18}$ taken together may form a ring being a substituted or unsubstituted, saturated or unsaturated cyclic structure;

each occurrence of $R_{19}$ and $R_{20}$ is independently a covalent bond that connects Si and C, an alkyl, substituted alkyl, or a heteroatom, wherein $R_{19}$ and $R_{20}$ optionally contain at least one heteroatom; wherein $L_1$-$L_2$ bonds with G through unsaturated sites $S_1$ and $S_2$;

each X is independently C1-C18 alkyl, C1-C18 substituted alkyl, aryl, or substituted aryl, wherein X optionally contains at least one heteroatom; and wherein the molar ratio of the Si—H functional groups in the silyl hydride to the alkenyl functional groups in the unsaturated compound is between about (0.5:α) and about (1.1:α).

2. The process of claim 1 wherein the molar ratio of the Si—H functional groups in the silyl hydride to the alkenyl functional groups in the unsaturated compound is about 1:α.

3. The process of claim 1 wherein the unsaturated compound is selected from the group consisting of trivinylcyclohexanes, trivinylbenzenes, tetravinylcyclobutane, trivinyltrimethylcyclotrisiloxane, tetramethyltetravinylcyclotetrasiloxane, triallylcyanurate, and triallylisocyanurate.

4. The process of claim 1 wherein the unsaturated compound is trivinylcyclohexane.

5. The process of claim 1, wherein the silyl hydride is selected from the group consisting of $R_aSiH_{4-a}$, $(RO)_aSiH_{4-a}$, $HSiR_a(OR)_{3-a}$, $R_3Si(CH_2)_f(SiR_2O)_eSiR_2H$, $(RO)_3Si(CH_2)_f(SiR_2O)_eSiR_2H$, $Q_uT_vT_p{}^HD_wD^H{}_xM^H{}_yM_z$, and combinations thereof, wherein Q is $SiO_{4/2}$, T is $R'SiO_{3/2}$, $T^H$ is $HSiO_{3/2}$, D is $R'_2SiO_{2/2}$, $D^H$ is $R'HSiO_{2/2}$, $M^H$ is $H_gR'_{3-g}SiO_{1/2}$, M is $R'_3SiO_{1/2}$, each occurrence of R and R' is independently C1-C18 alkyl, C1-C18 substituted alkyl, aryl, or substituted aryl, wherein R and R' optionally contain at least one heteroatom, each occurrence of a independently has a value from 1 to 3, f has a value of from 1 to 8, e has a value of from 1 to 11, g has a value of from 1 to 3, p is from 0 to 20, u is from 0 to 20, v is from 0 to 20, w is from 0 to 1000, x is from 0 to 1000, y is from 0 to 20, and z is from 0 to 20, provided that p+x+y equals 1 to 3000, and the valences of the all the elements in the silyl hydride are satisfied.

6. The process of claim 1 wherein the silyl hydride has one of the following structures: $R^3{}_3SiH$ (Formula VI), $HSi(OR^4)_3$ (Formula VII),

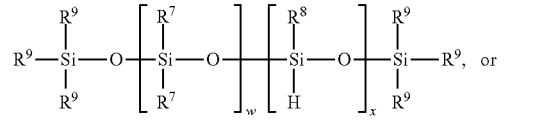

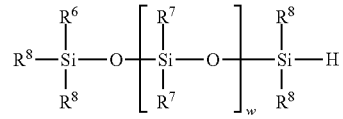

wherein each occurrence of $R^3$, $R^4$, $R^7$, $R^8$, and $R^9$ is independently a C1-C20 alkyl or an aryl group; $R^6$ is hydrogen, a C1-C20 alkyl or an aryl group; and x and w are independently greater than or equal to 0.

7. The process of claim 5 wherein the silyl hydride is selected from the group consisting of $(CH_3O)_3SiH$, $(C_2H_5O)_3SiH$, $(CH_3)_3SiOSi(CH_3)_2H$, $[(CH_3)_3SiO]_2SiH(CH_3)$, $[(CH_3)_2SiO]_3OSiH(CH_3)$, and $[(CH_3)_2SiO]_4OSiH(CH_3)$.

8. The process of claim 5 wherein the complex has a structural Formula (I), and wherein $R_{23}$ is

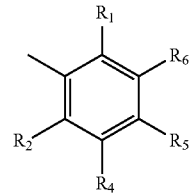

wherein $R_1$ and $R_2$ are both methyl, ethyl, propyl or isopropyl groups, and $R_4$, $R_5$, and $R_6$ are as defined in claim 1.

9. The process of claim 1 wherein the complex is immobilized on a support.

10. A process for selectively producing a mono-hydrosilylated product from 1,2,4-trivinylcyclohexane and a silyl hydride comprising reacting trivinylcyclohexane with the silyl hydride in the presence of a complex of Formula (I), Formula (II) or Formula (III), wherein Formula (I), Formula (II) and Formula (III) are as defined in claim 1;

wherein the molar ratio of the Si—H functional groups in the silyl hydride to the alkenyl functional groups in the 1,2,4-trivinylcyclohexane is between about (0.5:3) and about (1.1:3); and wherein the silyl group from the silyl hydride is selectively added to the 4 position of the 1,2,4-trivinylcyclohexane.

11. The process of claim 10 wherein the silyl hydride is triethoxysilane.

12. The process of claim 11 wherein the silyl hydride is bis(trimethylsiloxy)methylsilane.

13. The process of claim 10 wherein the trivinylcyclohexane is a mixture of trivinylcyclohexane stereoisomers.

14. The process of claim 10 wherein the 1,2,4-trivinylcyclohexane is 1,2,4-trivinylcyclohexane isomer A of Formula (XVI) and/or 1,2,4-trivinylcyclohexane isomer B of Formula (XVII)
(Formula XVI)
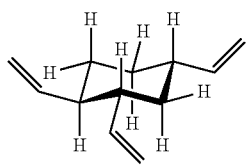
Isomer A
(Formula XVII)
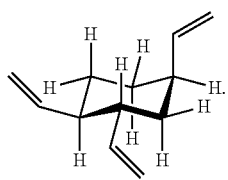
Isomer B
* * * * *